US011197747B2

(12) United States Patent
Macias-Harris (10) Patent No.: US 11,197,747 B2
(45) Date of Patent: Dec. 14, 2021

(54) LIGHT BRUSH AND METHOD OF USE

(71) Applicant: Logopedia Speech Therapy Services, PLLC, Chandler, AZ (US)

(72) Inventor: Judith M. Macias-Harris, Chandler, AZ (US)

(73) Assignee: LOGOPEDIA SPEECH THERAPY SERVICES PLLC, Chandler, AZ (US)

( * ) Notice: Subject to any disclaimer, the term of this patent is extended or adjusted under 35 U.S.C. 154(b) by 544 days.

(21) Appl. No.: 16/008,361

(22) Filed: Jun. 14, 2018

(65) Prior Publication Data

US 2018/0360580 A1   Dec. 20, 2018

Related U.S. Application Data

(60) Provisional application No. 62/519,345, filed on Jun. 14, 2017.

(51) Int. Cl.
*A61N 5/06* (2006.01)
*A61C 19/06* (2006.01)

(52) U.S. Cl.
CPC ............ *A61C 19/06* (2013.01); *A61N 5/0603* (2013.01); *A61C 2204/002* (2013.01); *A61N 2005/0606* (2013.01); *A61N 2005/0644* (2013.01); *A61N 2005/0652* (2013.01)

(58) Field of Classification Search
CPC ............. A61C 19/06; A61C 2204/002; A61N 5/0603; A61N 2005/0606; A61N 2005/0644; A61N 2005/0652
See application file for complete search history.

(56) References Cited

U.S. PATENT DOCUMENTS

| 8,021,148 B2 | 9/2011 | Goodson et al. | |
| 2007/0105063 A1* | 5/2007 | Pinyayev | A61N 5/0603 433/29 |
| 2008/0060148 A1* | 3/2008 | Pinyayev | A61B 5/415 15/22.1 |

OTHER PUBLICATIONS

Yin, R., Dai, T., Avci, P., Jorge, A.E.S., de Melo, W.C., Vecchio, D., Huang, Y.Y., Gupta, A. & Hamblin, M.R. (2013). "Light based anti-infectives: ultraviolet C irradiation, photodynamic therapy, blue light, and beyond. Current opinion in pharmacology, 13(5)"; http://www.sciencedirect.com/science/journal/14714892; Sep. 20, 2013; p. 731-762.

(Continued)

*Primary Examiner* — Ankit D Tejani
*Assistant Examiner* — Joshua Brendon Solomon
(74) *Attorney, Agent, or Firm* — Tarolli, Sundheim, Covell & Tummino LLP (57) ABSTRACT

A light device includes an elongated arm comprising a plurality of light emitting diodes ("LEDs") disposed at a first end of the elongated arm and configured to be positioned inside an oral cavity and to deliver one of a plurality of types of light treatments to the inside of the oral cavity according to a selected one of a plurality of operating modes. The light device further includes a body coupled to the elongated arm at a second end of the elongated arm. The body includes a battery for providing power to the LEDs. The body further includes a mode module coupled to the battery and the plurality of LEDs and configured to deliver power from the battery to at least one of the plurality of LEDS based on the selected operating mode.

19 Claims, 5 Drawing Sheets

(56) References Cited

OTHER PUBLICATIONS

R. Lubart et al.; "A Possible Mechanism for the Bactericidal Effect of Visible Light"; Article available at www.jstage.jst.go.jp/browse/islsm; Dec. 27, 2010; 6 pgs.

John F. O'Neill, BSc, et al.; "Oral Bacteria in Multi-Species Biofilms Can be Killed by Red Light in the Presence of Toluidine Blue"; Article-Lasers in Surgery and Medicine 31:86-90; Aug. 6, 2002; 5 pgs.

* cited by examiner

LIGHT BRUSH AND METHOD OF USE

CROSS-REFERENCE TO RELATED APPLICATION

This application claims priority from U.S. Patent Application No. 62/519,345 filed on Jun. 14, 2017, which is incorporated by reference herein in its entirety.

BACKGROUND

The oral cavity is the major reservoir for a variety of pathogens including bacteria, fungi and viruses. Dental plaque acts as a nucleus for bacteria and microorganisms that inhabit the enamel of teeth or gum line. Tongue-coating has also been associated as a risk indicator of aspiration pneumonia in edentate subjects.

Aggressive oral hygiene has been reported as being able to reduce pneumonia risk between 34-83% in high risk adults and appears to be an intervention method to reduce gastric and oral bacteria colonization. The Centers for Disease Control (CDC) has acknowledged the interplay between oral bacteria and health-care related pneumonia and stated that it was prudent for health-care facilities to implement a comprehensive oral-hygiene program. Education of health care workers to prevent pneumonias, interruption of transmission of microorganisms, and modifying host risk for infection have all received a CATEGORY 1A Grade by the U.S. Prevention Task Force. Dental caries is one of the most prevalent chronic diseases in the population worldwide, affecting 60-90% of school-aged children and almost 100% of the adult population.

Historically, implementing and being consistent with an oral care regimen in healthcare and home settings has been unsuccessful due to incomplete oral assessment tools, misconceptions on the importance of following oral care and hand hygiene, ineffective types of oral care products typically used in health care settings (e.g., swabs or sponges), patient resistance, "sensory-related" factors associated in special needs populations, and time.

SUMMARY

A light treatment device includes a light dome comprising a plurality of light emitting diodes ("LEDs") and configured to be positioned inside an oral cavity and to deliver a plurality of types of light treatments to the inside of the oral cavity. The light treatment device further includes an elongated arm coupled to the light dome at a first end of the elongated arm and configured to maintain the light dome inside the oral cavity while the light dome delivers the light treatment. The light treatment device further includes a body coupled to the elongated arm at a second end of the elongated arm. The body includes a battery for providing power to the LEDs. The body further includes an interface for receiving a selection of an operating mode corresponding to one of the plurality of types of light treatments. The light treatment device further includes a mode circuitry coupled to the battery, the interface, and the plurality of LEDs and configured to deliver power from the battery to at least one of the plurality of LEDS based on the selected operating mode.

A method for delivering light treatment to an oral cavity includes providing a light treatment device comprising light dome, the light dome comprising a plurality of light emitting diodes ("LEDs") and configured to be positioned inside an oral cavity and to deliver a plurality of types of light treatments to the inside of the oral cavity based on a selected mode of operation. The method further includes selecting a mode of operation of the light treatment device. The method further includes inserting the light treatment device into an oral cavity. The method further includes applying light treatment to the oral cavity based on the selected mode. The method further includes removing the light brush from the oral cavity.

A light device includes an elongated arm comprising a plurality of light emitting diodes ("LEDs") disposed at a first end of the elongated arm and configured to be positioned inside an oral cavity and to deliver one of a plurality of types of light treatments to the inside of the oral cavity according to a selected one of a plurality of operating modes. The light device further includes a body coupled to the elongated arm at a second end of the elongated arm. The body includes a battery for providing power to the LEDs. The body further includes a mode module coupled to the battery and the plurality of LEDs and configured to deliver power from the battery to at least one of the plurality of LEDS based on the selected operating mode.

BRIEF DESCRIPTION OF THE DRAWINGS

In the accompanying drawings, structures are illustrated that, together with the detailed description provided below, describe exemplary embodiments of the claimed invention. Like elements are identified with the same reference numerals. It should be understood that elements shown as a single component may be replaced with multiple components, and elements shown as multiple components may be replaced with a single component. The drawings are not to scale and the proportion of certain elements may be exaggerated for the purpose of illustration.

DETAILED DESCRIPTION

Low level laser therapy ("LLLT"), and similarly light emitting diodes ("LEDs"), is an example therapeutic modality for addressing oral bacteremia. A light brush described herein leverages LED technology to address bacteria/plaque build-up on the tongue, cheeks, and dental caries on teeth. The light brush is used intraorally to address oral tissue health by reducing signs and symptoms associated with bacteria, plaque and dental carries. The light brush was developed to provide an efficient instrument to help manage oral tissue health by reducing signs and symptoms associated with bacteria, plaque and dental carries for a large majority of populations and conditions. In particular, by using the light brush to apply different combinations of LED for different periods of time in order to deliver specific amounts of radiant energy, various conditions across various populations may be addressed in a cost-effective and efficient manner.

Figure 1:
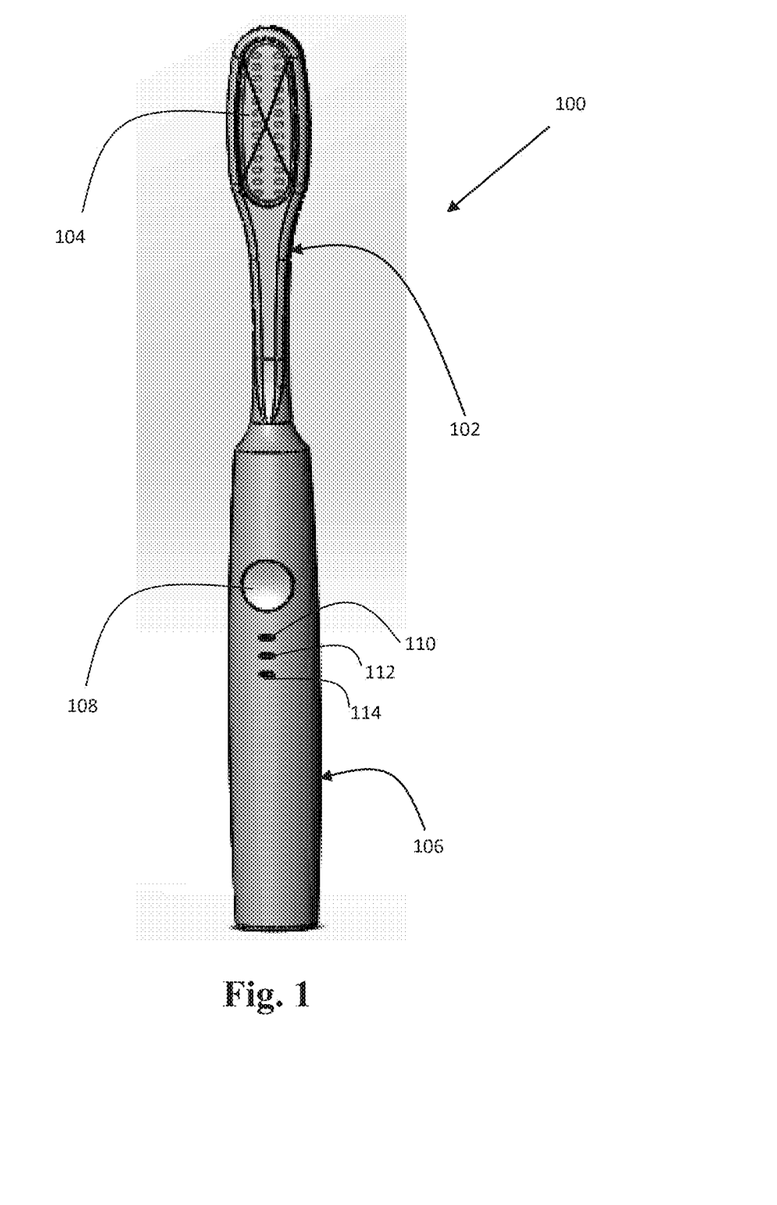
FIG. 1 illustrates an example light brush.

FIG. 1 illustrates an example light brush 100. The light brush 100 includes an arm 102 having a light dome 104 and configured to extend from a base 106 or a handle to aid in delivering light to a desired target location inside an oral cavity. In one example, the arm 102 is configured to be removable, thus being disposable and replaceable. For example, the arm 102 may be replaced if the light dome 104 of the arm 102 stops functioning as expected. In another example, the arm 102 may be interchanged with an alternate arm 102 having a light dome 104 capable of delivering an alternative light.

Figure 2:
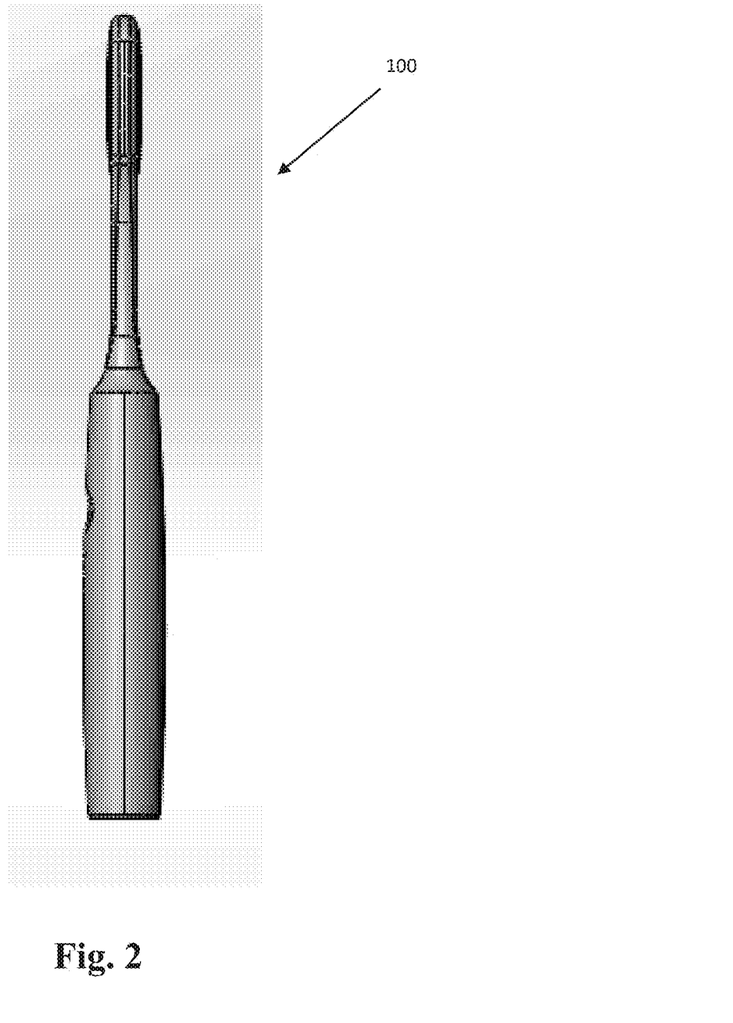
FIG. 2 illustrates an example side view of the example light brush of FIG. 1

The arm 102 in combination with light dome 104 is configured to be substantially flat, as illustrated in a profile view of the light brush 100 in FIG. 2. A flat profile enables the arm 102 and the light dome 104 to be positioned inside a target location of a patient's oral cavity while minimizing discomfort to the patient. The flat profile also enables gentle positioning of the arm 102 and the light dome 104 inside a target location when handling and maneuvering the light brush 100 via the base 106.

Referring back to FIG. 1, the light brush 100 further includes a power button 108 positioned on the handle 106 and configured to enable the light brush 100 to turn on an off. The light brush 100 includes a battery (not shown) to provide power. The battery may be removable, in one example. The battery may be rechargeable, in one example.

In one example, the light brush 100 is configured to deliver light in multiple modes, each mode being associated with a different combination of light sources, and thus a different treatment type. In one example, the light brush 100 provides a red light source and a blue light source via the light dome 104. The red light provides restorative action, healing and pain relief, while the blue light source helps eradicate surface bacteria, as measured by a pH level, and in particular to reduce the appearance of "tongue plaque" on the surface area of the tongue. Thus, the light brush 100 may be configured to deliver red light to a target location while operating in a first mode and to deliver blue light to the target location while operating in a second mode. In one example, the light brush 100 may be configured to deliver a combination of red light and blue light to the target location while operating in a third mode.

In one example, the light brush 100 includes a first LED light indicator 110 for indicating when the light brush 100 is operating in a first mode. The light brush 100 includes a second LED light indicator 112 for indicating when the light brush 100 is operating in a second mode. The light brush 100 includes a third LED light indicator 114 for indicating when the light brush 100 is operating in a third mode. It should be appreciated that although three LED light indicators 110, 112, and 114 are illustrated, the light brush 100 may include any suitable number of LED light indicators corresponding to the number of modes which the light brush 100 is configured to operate in. In one example, the LED light indicators 110, 112, and 114 may also function as push buttons for selecting the corresponding operating modes of the light brush 100. In one example, the power button 108 may be configured to enable selection of an operating mode. For example, pushing the power button 108 once may turn the light brush 100 on, while pushing the power button 108 after the light brush 100 is powered on may enable cycling through the different operating modes.

Figure 3:
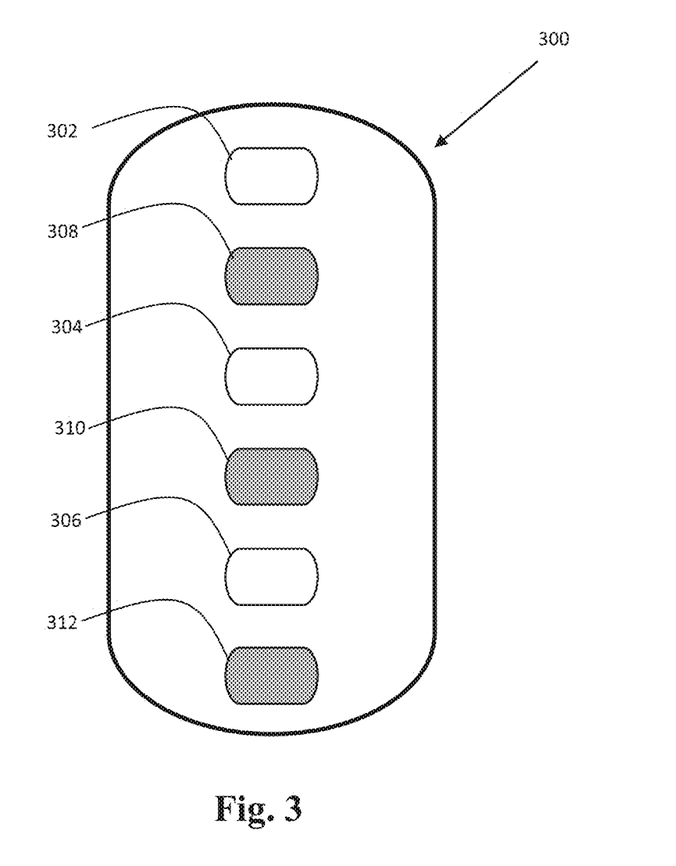
FIG. 3 illustrates a front view of an example light dome of an example light brush.

To enable different operating modes, the light dome 104 is configured to include a plurality of LED light sources. FIG. 3 illustrates a front view 300 of an example light dome, such as the light dome 100 of FIG. 1. The front view 300 includes six light sources 302, 304, 306, 308, 310, and 312. A rear view (not shown) has an identical layout including six additional light sources, for a total of 12 light sources. Thus, the example light dome is a front-to-back light dome meaning it exposes light sources on both the front side and the back side.

In particular, the example light dome includes three red light sources and three blue light sources on the front side 300, all arranged vertically. More particularly, the light dome includes a first red LED light source 302 near the top of the front side 300. A first blue LED light source 308 is positioned below the first red LED light source 302. A second red LED light source 304 is positioned below the first blue LED light source 308. A second blue LED light source 310 is positioned below the second red LED light source 304. A third red LED light source 306 is positioned below the second blue LED light source 310. A third blue LED light source 312 is positioned below the third red LED light source 306.

A back side (not shown) is a mirror image of the front side 300 and includes an identical arrangement of LED light sources. It should be appreciated that the arrangement of LEDs described is one example embodiment. A light dome, such as the light dome 104 of FIG. 1 may include any suitable number and arrangement of LEDs.

While operating in first mode of operation, the red LED light sources 302, 304, and 306 on the front side 300, as well as the red LED light sources on the back side (not shown), are turned on to emit light while the blue LED light sources 308, 310, and 312 on the front side 300, as well as the blue LED light sources on the back side (not shown), are turned off. While operating in second mode of operation, the red LED light sources 302, 304, and 306 on the front side 300, as well as the red LED light sources on the back side (not shown), are turned off while the blue LED light sources 308, 310, and 312 on the front side 300, as well as the blue LED light sources on the back side (not shown), are turned on to emit light. While operating in a third mode of operation, all 12 LED light sources, including the red LED light sources 302, 304, and 306 on the front side 300, the blue LED light sources 308, 310, and 312 on the front side 300, as well as the red and blue LED light sources on the back side (not shown), are turned on to emit light.

It should be appreciated that the red LED light sources 302, 304, and 306 on the front side 300, the blue LED light sources 308, 310, and 312 on the front side 300, as well as the red and blue LED light sources on the back side (not shown), may be turned on and off in any suitable combination in while operating in alternative operating modes not described herein.

Thus, by adjusting the mode of operation, the light brush 100 can be configured to either to provide pain relief and treatment of inflammation, to provide treatment to eradicate surface bacteria, and to reduce the appearance of "tongue plaque" on the surface area of the tongue. By incorporating red/blue light sources on both the front and back of the light dome 300, the light brush is able to more effectively deliver light to a desired target location. In one example, the light dome 300 is configured to emit light from the front side 300 and the back side simultaneously.

In one example, the blue LED light sources 308, 310, and 312 emit a 415 nm blue. In one example, the red LED light sources 302, 304, and 306 emit a 660 nm red. In one example, the light brush 100 is configured to emit a combined light at 1 $J/cm^2$. In one example, the treatment intensity may be adjusted by turning on only a portion of the light sources.

In another example, the treatment intensity may be adjusted by controlling the length of time the light brush 100 emits light to a target location. In one example, the light brush 100 may include a time (not shown) to time the amount of time light is being delivered to a target location. In one example, the light brush 100 may include a user feedback mechanism (not shown) such an LED indicator or a vibration to notify a user when a desired length of time of treatment has been reached, indicating to turn off the light brush 100. In one example, the light brush 100 may be configured to automatically turn off and to stop emitting light upon the timer reaching the desired length of time of treatment.

It should be appreciated that, although the example light dome 300 is illustrated to include three red LED light sources 302, 304, and 306, and three blue LED light sources 308, 310, and 312 arranged in a vertical alternating pattern on the front side 300, and another three red LED light sources and three blue LED light sources arranged in a vertical alternating pattern on the back side (not shown), another example of a light dome (not sown) may include any suitable number of light sources, including any suitable combination of colors of light sources, arranged in any suitable pattern.

It should be appreciated that although the example light brush 100 describe herein may resemble a traditional tooth brush, the light brush 100 does not include bristles as a traditional tooth brush. Accordingly, the light brush 100 provides waterless treatment with no bristles or specialized toothpaste simultaneous to providing light treatment to the global target region inside the oral cavity.

It should be appreciated that, although the example light brush 100 is described herein with a configuration of LED light sources for treating pain eradicate surface bacteria, and reduce the appearance of "tongue plaque" on the surface area of the tongue within an oral cavity, the light brush 100 may be configured with LED light sources for performing additional or alternative functions. For example, the light brush 100 may be configured with LED light sources for improving circulation and oxygenation in the oral cavity of a patient.

Figure 4:
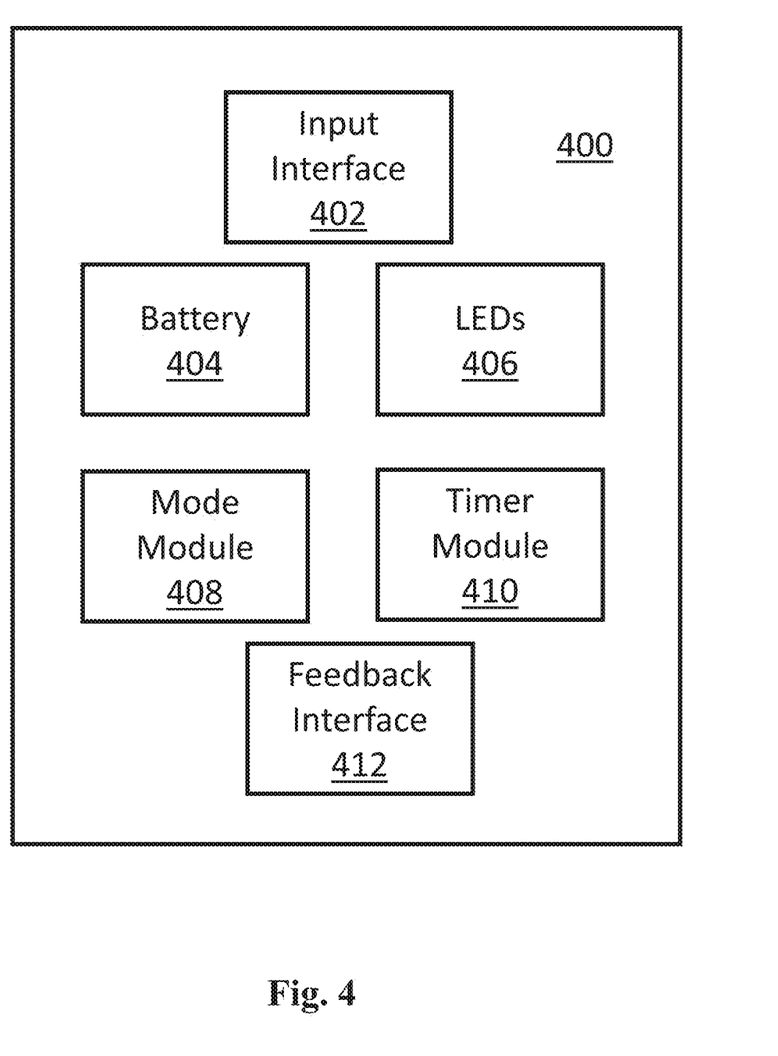
FIG. 4 illustrates a block diagram of an example light brush.

FIG. 4 illustrates a block diagram of an example light brush 400, such as the light brush 100 of FIG. 1. The light brush 400 includes an input interface module 402 for receiving input from a user. Input may include, for example, request to power the light brush 400 on or off or to switch operating modes of the light brush 400. The input interface module 402 may include one or more buttons, for example, or other suitable mechanisms for receiving user input.

The light brush 400 includes an LED light source 406 for providing light treatment to a patient. The light brush includes a battery 404 for powering the LED light source 406. The battery 404 may be rechargeable in one example. The battery 404 may be removable in one example. The LED light source 406 may include any suitable combination of LEDS and colors of light sources. In one example, the LED light source 406 includes six 415 nm blue LEDs and six 660 nm red LEDs.

The light brush 400 includes a mode module 408 configured to turn on and off the LED light source 406 according to a mode provided by the input interface 402. The mode module 408 may include circuitry coupled to the battery 404 and configured to deliver power to the LED light source 406 from the battery according to the provided mode. In one example, the light brush 400 includes a timer module 410 configured to keep track of the amount of time that the LED light source 406 is emitting light for a given treatment. The timer module 410 may be configured to reset automatically upon the light brush 400 being powered on or off or upon the mode module 408 changing a mode of the light brush 400, for example.

The light brush 400 includes a feedback interface module 412 configured to provide user feedback. User feedback may include, for example, indication of a current mode of operation of the light brush 400 or the expiration of a desired treatment time as determined by the timer module 410. The feedback interface module may include an LED display, a vibration device, a speaker for providing an audible feedback, or another suitable mechanism for providing user feedback.

Figure 5:
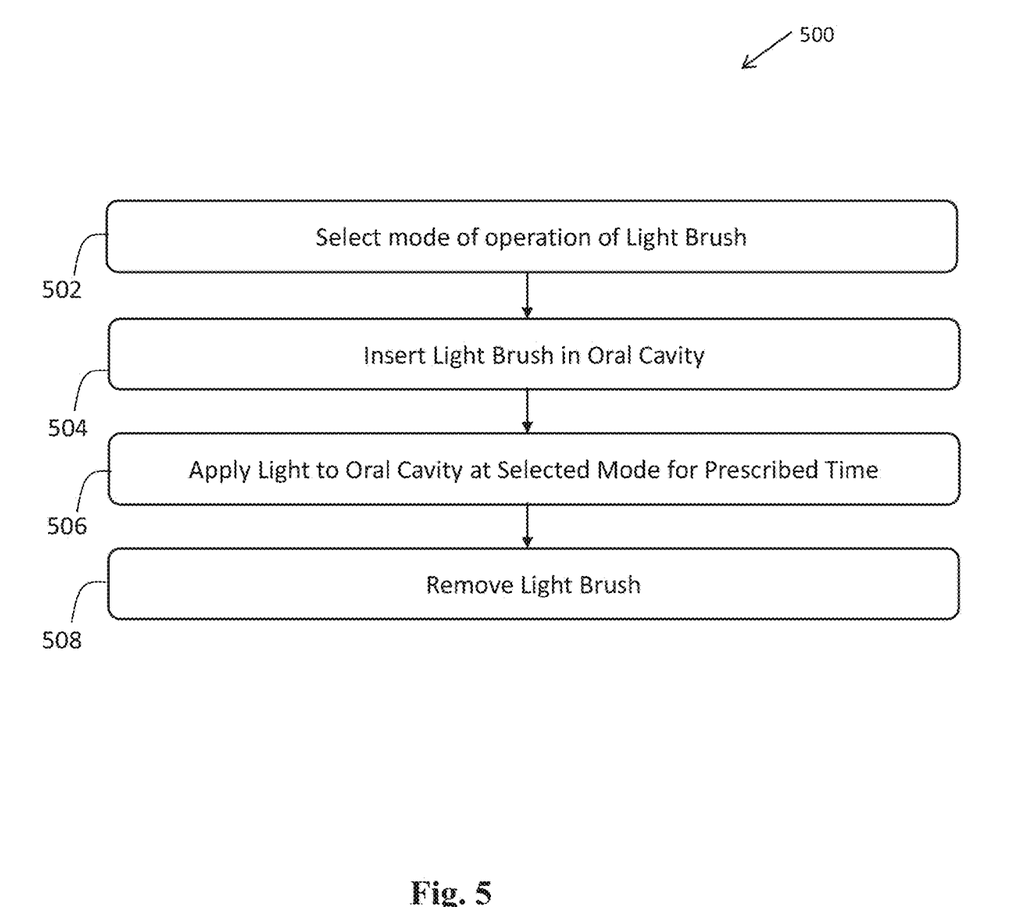
FIG. 5 illustrates an example method for using an example light brush.

FIG. 5 illustrates a method for using a light brush, such as the light brush 100 of FIG. 1. At 502, a mode of operation for of the light brush is selected. In one example, a mode also includes a prescribed time for administering the light treatment to the patient. A mode may be selected via an input interface, such as the input interface module 402 of FIG. 4. A mode may be selected according to various factors. For example, depending on whether the intent is to treat a target area to improve the appearance of the surface area of tongue or to improve pH of the oral cavity will dictate the selection of the operating mode of the light brush, and in particular the type(s) of light to be delivered to the target area. The age and type of patient may also dictate the selection of the operating mode. For example, a child patient may require treatment for a shorter duration of time in order to achieve desired results as compared to a duration of time required for treating an adult patient to achieve the desired results. Moreover, the severity of a condition may also dictate the treatment mode. Additionally, maintenance of an oral cavity may require a different operation mode as compared to treatment of a condition of an oral cavity.

At 504, the light brush is inserted in an oral cavity of a patient and positioned such that light from a light dome of the light brush is directed towards a target location inside the oral cavity. At 506, the light brush is turned on and light is delivered to the target area at the selected mode for a prescribed length of time. In one example, an ideal length of time for delivering light to a target area is in a range between 15-60 seconds. Thus, between 15-60 J/cm$^2$ of light is delivered as part of a treatment. At 508, once the prescribed treatment time has expired, the light brush is removed from the oral cavity.

In one example, a treatment protocol may require multiple light treatments over the course of a day or multiple days. Thus, in one example, the method 500 described herein may be repeated as needed according to a prescribed frequency.

In one example, selecting a mode of operation comprises determining a severity level or a risk factor associated with an oral cavity condition for a particular patient. The determined severity levels may be translated to an overall risk factor score, which may then be used to determine a treatment protocol. For example, a patient may be assigned a first score, or range of scores, if the patient is determined to have zero to very little risk factors associated with an oral cavity condition. The patient may be assigned a second score, or range of scores, if the patient is determined to have mild risk factors associated with the oral cavity condition. A patient may be assigned a third score, or range of scores, if the patient is determined to have severe risk factors associated with the oral cavity condition. Factors used to assess a patient and determine a score may include, for example: determining a level of care, including measuring dependency for feeding, dressing, and mobility; determining cognitive/health status, including measuring areas that contribute to level of "alertness", physiological factors (e.g., respiration/digestion); swallowing function; and interventions that present with global, pre/post static change (e.g., post effects of RX, CA, alcohol/tobacco abuse); determing pH of the Oral Cavity, including measuring acidic vs alkaline levels across areas (e.g., cheeks, gumline, tongue); and determining an oral/dental status, including measuring conditions of the oral cavity (e.g., tooth/tongue plaque; tissue and teeth conditions; saliva output).

The mode of operation of the light brush, and therefore the protocol for treating the patient with the light brush may be adjusted according to the determined score. For example, Table 1 illustrates example protocols for using a light brush, such as the light brush 100 of FIG. 1, for treating a patient with a moderate risk factor score associated with aspiration pneumonia, while Table 2 illustrates example protocols for using a light brush, such as the light brush 100 of FIG. 1, for treating a patient with a severe risk factor score associated with aspiration pneumonia.

TABLE 1

Protocols for using a light brush for treating a patient with a moderate risk factor score associated with aspiration pneumonia.

| Population | Setting | Instructions/Duration | Frequency | Example Schedule | Maintenance |
| --- | --- | --- | --- | --- | --- |
| Child (6 years or older) or fragile teen/adult | #3: Red/Blue combo | Place the device in the mouth. Ensure that the flat head hovers over the tongue area and the neck of the device rests between the teeth. Close the lips and run the device for 60 seconds. Do this one time a day, preferably in the morning. | 1-2 times a week. It is recommended to wait 1-2 days between applications. | Sunday: Red/Blue combo (AM or PM) Monday: No application Tuesday: No application Wednesday: Red/Blue combo (AM or PM) Thursday: No application Friday: No application Saturday: Reassess for global Oral/dental scores. | When global Oral/Dental scores reduce to .9 or lower, it is recommended to use this setting one time a day, 1-2 time a week for maintenance. If the global Oral/Dental score does not change, continue with this schedule until the global score is .9 or lower. When global Oral/Dental scores reduce to .9 or lower, it is recommended to use this setting one time a day once a week for maintenance. |
| Adult (18 years and older) | #3: Red/Blue Combo | Place the device in the mouth. Ensure that the flat head hovers over the tongue area and the neck of the device rests between the teeth. Close the lips and run the device for 60 seconds. Do this 1-2 times a day, preferably in the morning and evening. | 2-3 times a week. Wait 1-2 days between treatment | Sunday: Red/Blue combo (AM or PM) Monday: No application Tuesday: Red/Blue combo (AM or PM) Wednesday: No application Thursday: Red/Blue combo (AM or PM) Friday: No application Saturday: Reassess for global Oral/dental scores. | When global Oral/Dental scores reduce to .9 or lower, it is recommended to use this setting one time a day, 1-2 time a week for maintenance. If the global Oral/Dental score does not change, continue with this schedule until the global score is .9 or lower. When global Oral/Dental scores reduce to .9 or lower, it is recommended to use this setting one |

TABLE 1-continued

Protocols for using a light brush for treating a patient with a moderate risk factor score associated with aspiration pneumonia.

| Population | Setting | Instructions/Duration | Frequency | Example Schedule | Maintenance |
|---|---|---|---|---|---|
| | | | | | time a day, 1-2 time a week for maintenance. |

TABLE 2

Protocols for using a light brush for treating a patient with a severe risk factor score associated with aspiration pneumonia.

| Population | Setting | Instructions/Duration | Frequency | Example Schedule | Maintenance |
|---|---|---|---|---|---|
| Child (6 years or older) or fragile teen/adult | #1: Blue (1-2 times a week) #2 Red: (1-2 times a week) | Place the device in the mouth. Ensure that the flat head hovers over the tongue area and the neck of the device rests between the teeth. Close the lips and run the device for 60 seconds. Do this two (2) time a day, preferably in the morning and evening. | It is recommended to wait one day to apply the red application after using the blue application and vice-versa. | Sunday: Blue (AM)/Blue (PM) Monday: No application Tuesday: Red (AM)/Red (PM) Wednesday: No application Thursday: Blue (AM)/Blue (PM) Friday: No application Saturday: Red (AM)/Red (PM) Recalculate for the global Oral/Dental score to determne next course of action. | When global Oral/Dental scores reduce to 1.5 or lower, change the LightBrush setting to #3. It is recommended to use this setting one time a day, 1-2 times a week, with a "rest" a day in between. If the global Oral/Dental score does not change, continue one more week with the initial settings, frequency, and schedule. When global Oral/Dental scores reduce to 1.5 or lower, change the LightBrush setting to #3. It is recommended to use this setting one time a day, 1-2 times a week, with a "rest" a day in between. |
| Adult (18 years and older) | #1: Blue (1-2 times a week) #2 Red: (1-2 times a week) | Place the device in the mouth. Ensure that the flat head hovers over the tongue area and the neck of the device rests between the teeth. Close the lips and run the device for 60 seconds. Do this two (2) times a day, preferably in the morning and evening. | It is recommended to wait one day to apply the red application after using the blue application and vice-versa. | Sunday: Blue (AM)/Blue (PM) Monday: No application Tuesday: Red (AM)/Red (PM) Wednesday: No application Thursday: Blue (AM)/Blue (PM) Friday: No application | When global Oral/Dental scores reduce to 1.5 or lower, change the LightBrush setting to #3. It is recommended to use this setting one time a day, 1-2 times a |

TABLE 2-continued

Protocols for using a light brush for treating a patient with a severe risk factor score associated with aspiration pneumonia.

| Population | Setting | Instructions/Duration | Frequency | Example Schedule | Maintenance |
|---|---|---|---|---|---|
| | | | | Saturday: Red (AM)/Red (PM) Recalculate for the global Oral/Dental score to determine next course of action. | week, with a "rest" a day in between. If the global Oral/Dental score does not change, continue one more week with the initial settings, frequency, and schedule. When global Oral/Dental scores reduce to 1.5 or lower, change the LightBrush setting to #3. It is recommended to use this setting one time a day, 1-2 times a week, with a "rest" a day in between. |

To the extent that the term "includes" or "including" is used in the specification or the claims, it is intended to be inclusive in a manner similar to the term "comprising" as that term is interpreted when employed as a transitional word in a claim. Furthermore, to the extent that the term "or" is employed (e.g., A or B) it is intended to mean "A or B or both." When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2d. Ed. 1995). Also, to the extent that the terms "in" or "into" are used in the specification or the claims, it is intended to additionally mean "on" or "onto." Furthermore, to the extent the term "connect" is used in the specification or claims, it is intended to mean not only "directly connected to," but also "indirectly connected to" such as connected through another component or components.

While the present application has been illustrated by the description of embodiments thereof, and while the embodiments have been described in considerable detail, it is not the intention of the applicants to restrict or in any way limit the scope of the appended claims to such detail. Additional advantages and modifications will readily appear to those skilled in the art. Therefore, the application, in its broader aspects, is not limited to the specific details, the representative apparatus and method, and illustrative examples shown and described. Accordingly, departures may be made from such details without departing from the spirit or scope of the applicant's general inventive concept.

What is claimed:

1. A light treatment device, comprising:
a light dome comprising a plurality of light emitting diodes ("LEDs") and configured to be positioned inside an oral cavity and to deliver a plurality of types of light treatments to the inside of the oral cavity;
an elongated arm coupled to the light dome at a first end of the elongated arm, wherein the light dome and elongated arm have a flat profile without bristles or other structure protruding from the light dome to facilitate insertion thereof into the oral cavity and enable gentle positioning thereof while minimizing discomfort to the patient, and the elongated arm is configured to maintain the light dome inside the oral cavity while the light dome delivers the light treatment inside the oral cavity with the light dome spaced from tissue inside the oral cavity during such treatment; and
a body coupled to the elongated arm at a second end of the elongated arm, the body comprising:
a battery for providing power to the LEDs;
an interface for receiving a selection of an operating mode corresponding to one of the plurality of types of light treatments; and
a mode circuitry coupled to the battery, the interface, and the plurality of LEDs and configured to deliver power from the battery to at least one of the plurality of LEDS based on the selected operating mode.

2. The light treatment device of claim 1, wherein the plurality of types of light treatments comprise a pain relief treatment.

3. The light treatment device of claim 1, wherein the plurality of types of light treatments comprise a treatment for improving pH level inside the oral cavity.

4. The method of claim 1, wherein the plurality of types of light treatments comprise a treatment for reducing the appearance of tongue plaque on a surface area of a tongue.

5. The light treatment device of claim 1, wherein the plurality of LEDs comprises at least one 415 nm blue LED and at least one 660 nm red LED.

6. The light treatment device of claim 5, wherein the plurality of LEDs comprises a pattern of alternating 415 nm blue LEDs and 660 nm red LEDs.

7. The light treatment device of claim 5, wherein the plurality of LEDs comprises six 415 nm blue LEDs and six 660 nm red LEDs.

8. The light treatment device of claim 1, wherein the light treatment device is configured to emit a combined light at 1 J/cm$^2$.

9. The light treatment device of claim 1, wherein the light dome comprises a first plurality of LEDs on a front side and a second plurality of LEDs on a rear side.

10. The light treatment device of claim 1, wherein the interface comprises a plurality of LEDs configured to indicate the selection of the operating mode.

11. A light device, comprising:
an elongated arm comprising a plurality of light emitting diodes ("LEDs") disposed at a first end of the elongated arm, wherein the elongated arm has a flat profile without bristles or other structure protruding from the elongated arm to facilitate insertion thereof into the oral cavity and enable gentle positioning thereof while minimizing discomfort to the patient, and the elongated arm is configured to be positioned inside an oral cavity and to deliver one of a plurality of types of light treatments to the inside of the oral cavity with the first end of the elongated arm spaced from tissue during delivery of such treatment according to a selected one of a plurality of operating modes;
a body coupled to the elongated arm at a second end of the elongated arm, the body comprising:
a battery for providing power to the LEDs; and
a mode module coupled to the battery and the plurality of LEDs and configured to deliver power from the battery to at least one of the plurality of LEDS based on the selected operating mode.

12. The light device of claim 11, wherein the plurality of LEDs form a light dome to deliver the light treatment, and wherein the body further comprises an interface that includes one or more buttons for receiving an input to select the selected operating mode corresponding to one of the plurality of types of light treatments.

13. The light treatment device of claim 9, wherein the first plurality of LEDs on the front side of the light dome comprise at least one 415 nm blue LED and at least one 660 nm red LED and the second plurality of LEDs on the rear side of the light dome comprise at least one 415 nm blue LED and at least one 660 nm red LED.

14. The light treatment device of claim 1, wherein the interface includes a button to receive a user input to select one of a plurality of operating modes corresponding to respective types of light treatments.

15. The light treatment device of claim 14, wherein the plurality operating modes comprises a first mode to provide 660 nm red light treatment, a second mode to provide 415 nm blue light treatment and a third mode to provide both 660 nm red light and 415 nm blue light treatment.

16. The light device of claim 11, wherein the first end of the elongated arm has opposing first and second sides in which a first plurality of LEDs are on the first side and a second plurality of LEDs on the second side.

17. The light device of claim 16, wherein the first plurality of LEDs on the first side comprises at least one 415 nm blue LED and at least one 660 nm red LED and the second plurality of LEDs on the second side comprises at least one 415 nm blue LED and at least one 660 nm red LED.

18. The light treatment device of claim 12, wherein the plurality operating modes comprises a first mode to provide 660 nm red light treatment, a second mode to provide 415 nm blue light treatment and a third mode to provide both 660 nm red light and 415 nm blue light treatment.

19. A light treatment device comprising:
an elongated arm includes a flat head at a distal end of the elongated arm adapted to be positioned inside an oral cavity, the flat head having opposing side surfaces and configured to provide a flat profile without bristles or other structure protruding from the flat head to facilitate insertion of the flat head and a portion of the elongated arm into the oral cavity and enable gentle positioning thereof while minimizing discomfort to the patient;
a plurality of light emitting diodes ("LEDs") disposed on the at least one of the side surfaces of the flat head, the LEDs configured to deliver at least one type of light treatment inside the oral cavity while the LEDs are spaced from tissue inside the oral cavity during such treatment;
a body extending from a proximal end of the elongated arm, the body comprising:
a battery for providing power to the LEDs;
an interface configured to select one of a plurality of operating modes in response to a user input, each of the operating modes corresponding to a respective type of light treatment; and
a mode module coupled to the battery and the interface, the mode module configured to control delivery power from the battery to at least one of the plurality of LEDs based on the selected operating mode.

* * * * *